United States Patent [19]

Bailey

[11] 4,190,050
[45] Feb. 26, 1980

[54] TREPHINE INSTRUMENT FOR USE IN CORNEA REMOVAL AND TRANSPLANT

[76] Inventor: Paul F. Bailey, 4885 NW. Barnes Rd., Portland, Oreg. 97210

[21] Appl. No.: 819,884

[22] Filed: Jul. 28, 1977

[51] Int. Cl.$^2$ ............................................... A61B 17/16
[52] U.S. Cl. ................................. 128/305.1; 30/123.5; 30/125; 30/130; 30/44
[58] Field of Search ............... 128/310, 305 R, 2 B, 128/2 T, 329 R, 303 C, 305.1; 30/123.6, 123.5, 125, 130, 44, 48, 63, 362

[56] References Cited

U.S. PATENT DOCUMENTS

| | | | |
|---|---|---|---|
| 2,504,075 | 4/1950 | Karle | 128/310 |
| 2,598,060 | 5/1952 | Kadesky | 128/305 |
| 2,838,050 | 6/1958 | Ara | 128/310 |
| 3,074,407 | 1/1963 | Moon et al. | 128/310 X |
| 3,927,675 | 12/1975 | Pohlman et al. | 128/328 |

Primary Examiner—Henry J. Recla
Attorney, Agent, or Firm—Kolisch, Hartwell, Dickinson & Stuart

[57] ABSTRACT

A trephine instrument for use in surgical removal of a cornea includes a cylindrical blade mounted on an elongate handle. The blade is power-driven and an actuating element is operable for selectively extending and retracting the blade. In a second embodiment, an ultrasonic source powers the blade. Further, the blade is detachably connected to the handle so that it may serve as a storage container for a cornea. In both embodiments, the handle includes offset portions so that a surgeon may grip the instrument with both hands and position the blade adjacent an eye.

16 Claims, 8 Drawing Figures

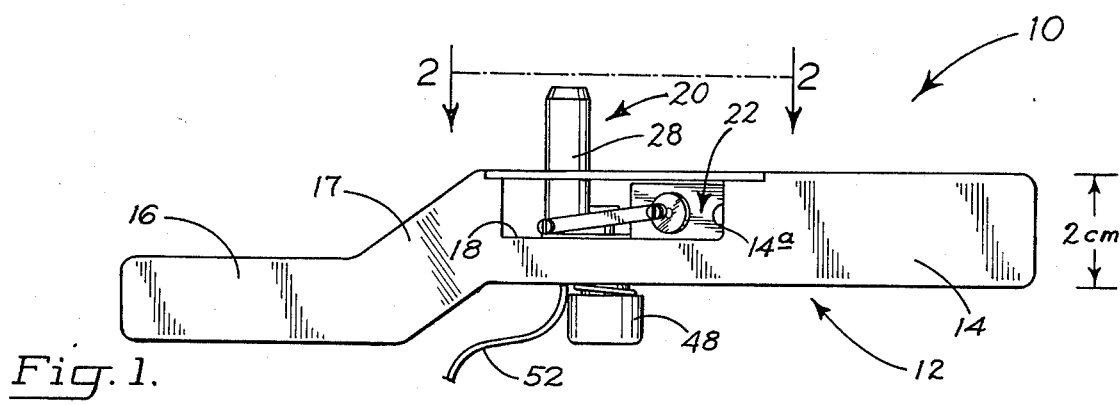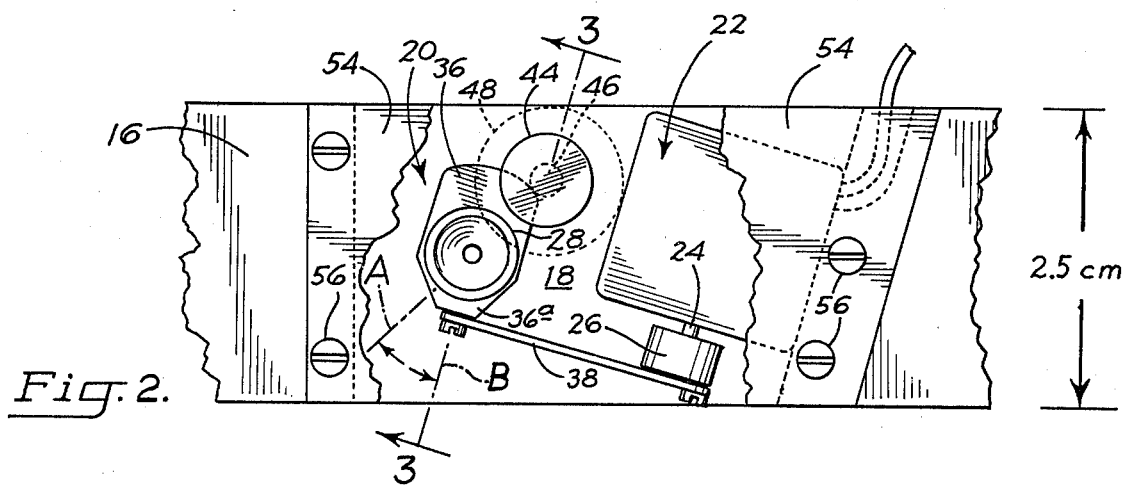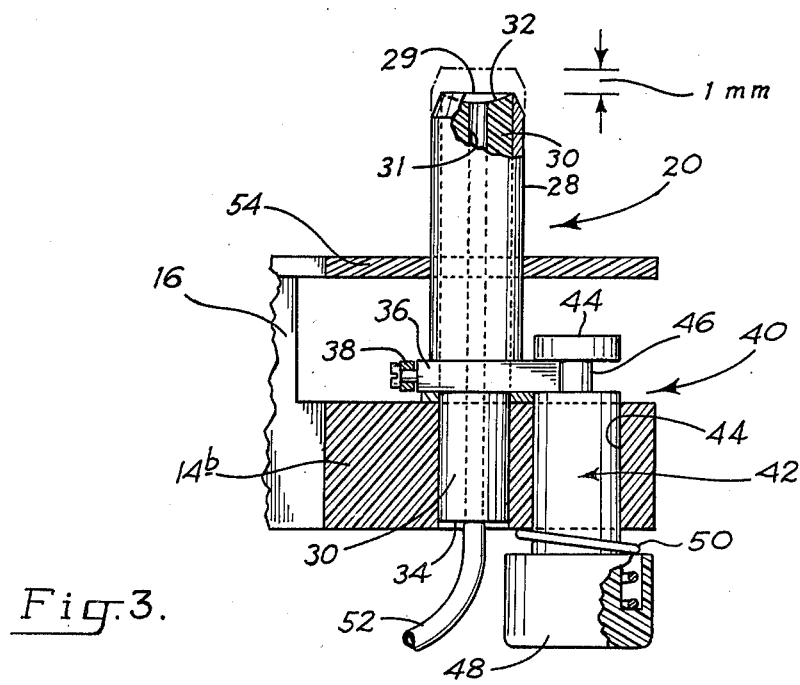

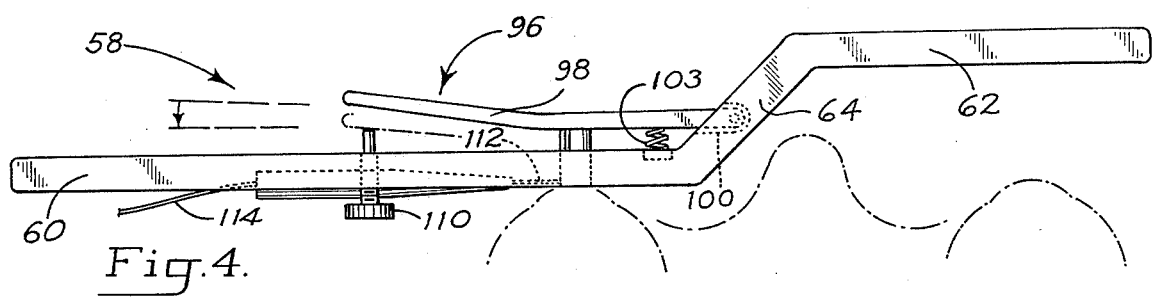
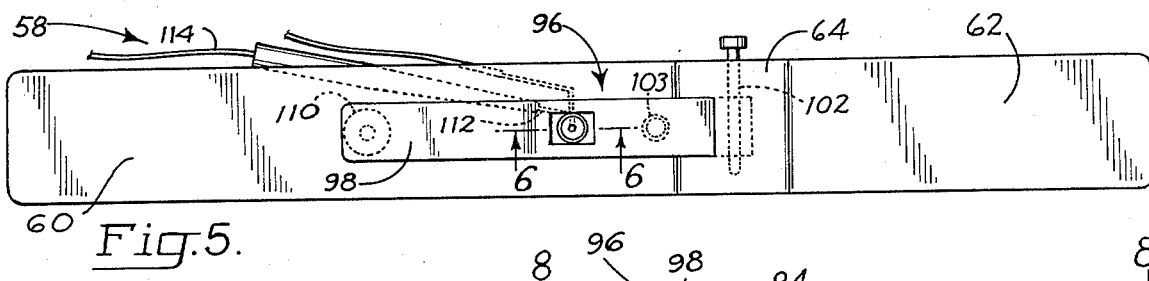
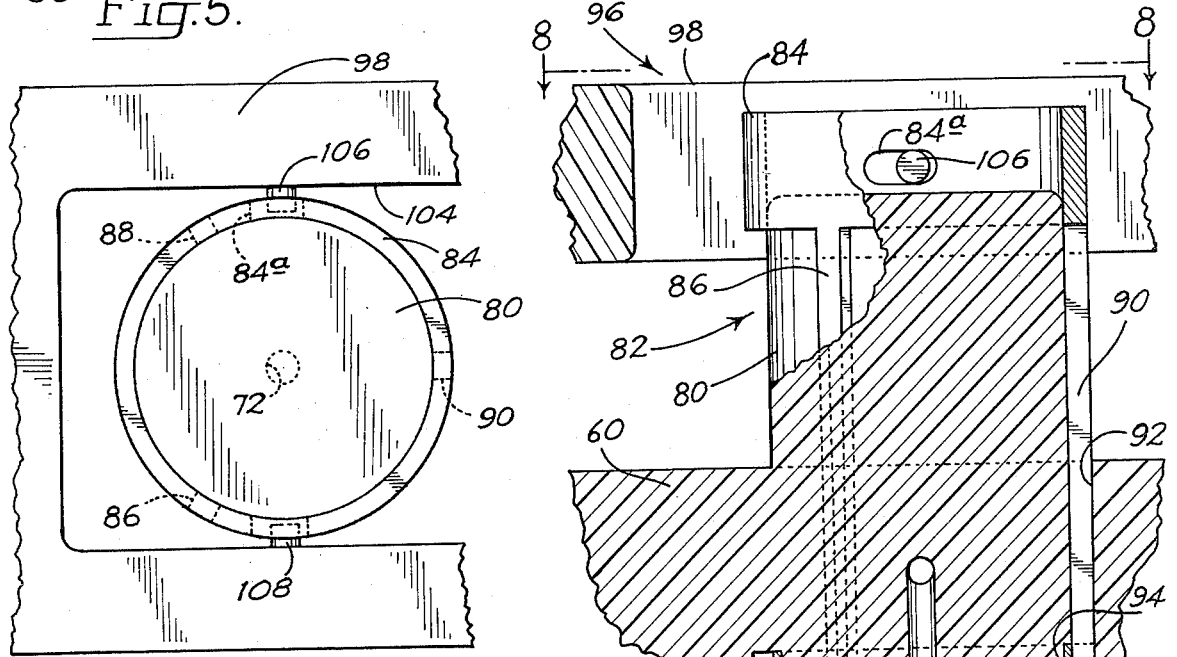
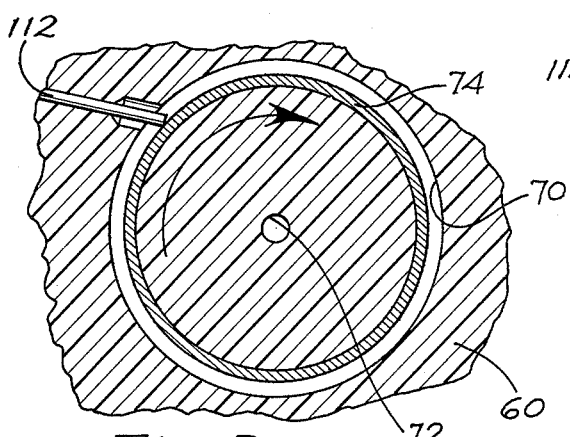

TREPHINE INSTRUMENT FOR USE IN CORNEA REMOVAL AND TRANSPLANT

BACKGROUND AND SUMMARY OF THE INVENTION

The present invention relates to surgical instruments, and more particularly to corneal trephine instruments used in the removal and grafting of corneal "buttons."

Corneal transplants may be required for a variety of medical reasons. For instance, through accident, disease or old age, an individual's cornea may become occluded or otherwise impaired. Light rays are then substantially prevented from reaching the lens thus causing blindness or varying degrees of blindness. A method for alleviating blindness caused by defective corneas is the corneal transplant.

In a transplanting operation, the first step is to remove a corneal button from a deceased donor. An occluded or otherwise defective corneal button is then removed from a recipient and the corneal button from the donor is transplanted and sutured into position for grafting.

Various types of instruments are used presently by surgeons in removing corneal buttons. Prior art trephine instruments generally comprise a cylindrical cutting member having an annular blade. A surgeon must manually rotate the cutting member about its longitudinal axis in order to effect cutting action. It can be readily appreciated that considerable skill and dexterity is required in order for the surgeon to make a precise and uniform incision through the thickness of a cornea.

Prior art trephine instruments may require the surgeon to use a small table or bench on which to steady his hands. Even with the use of such a table, it is still extremely difficult for even a skilled surgeon to impart cutting action and maintain alignment during cutting of the cornea.

Accordingly, it is a general object of the present invention to provide a trephine instrument having a power-driven cutting blade mounted on an elongate handle which may be firmly gripped with both hands of a surgeon. The elongate handle includes first and second handle portions having their longitudinal axes offset from each other. A connecting handle portion provides a diagonal or offset which may extend over the nose bridge of the individual being operated upon.

Another object of the present invention is to provide a trephine instrument in which the power-driven cutting blade may be accurately and precisely extended and retracted relative to the handle. To this end, a simplified digital-operated shifting mechanism is appropriately provided.

Still another object of the present invention is to provide a trephine instrument in which the cutting blade is mounted on a guide formed of clear material, such as plastic, so the surgeon can clearly view cutting action on the cornea.

Yet another object of the present invention, in a second embodiment, is to provide a trephine instrument in which the cutting blade is readily removable so that it can serve as a storage container for a removed corneal button. It is contemplated that the blade may be quickly capped on both ends to form a closed, sterile container.

A yet further object of the present invention is to provide a trephine instrument in which the cutting blade is actuated by an ultrasonic source to effect cutting action.

These and additional objects of the present invention reside in the specific construction of the preferred embodiments hereinafter particularly described in the specification and shown in the several drawings.

BRIEF DESCRIPTION OF THE DRAWINGS

FIG. 1 is a side elevation view of a first embodiment of a trephine instrument in accordance with the principles of the present invention;

FIG. 2 is an enlarged, top plan view, partially broken away, taken along lines 2—2 of FIG. 1;

FIG. 3 is a side elevation view, partially broken away, taken along lines 3—3 of FIG. 2 and illustrates details of a cutting blade and actuating element for shifting the blade;

FIG. 4 is a side elevation view of a second embodiment of the present invention illustrating positioning of the trephine instrument adjacent to an eye from which a corneal button is to be removed;

FIG. 5 is a top plan view of the trephine instrument illustrated in FIG. 4;

FIG. 6 is an enlarged, side elevation view, partially broken away, taken along lines 6—6 of FIG. 5;

FIG. 7 is a cross-sectional view, partially broken away, taken along lines 7—7 of FIG. 6; and FIG. 8 is a top plan view, partially broken away, taken along lines 8—8 of FIG. 6.

DETAILED DESCRIPTION OF THE PREFERRED EMBODIMENTS

Turning now to the drawings, and referring initially to FIGS. 1-3, a trephine instrument, according to a first embodiment of the present invention, is designated at 10. Instrument 10 includes an elongate handle means, generally designated at 12, which includes first and second handle portions 14, 16, respectively. The first and second handle portions are joined together by a diagonal such as interconnecting portion 17 so that their longitudinal axes are offset from each other. More specifically, handle portion 14 is laterally spaced and longitudinally offset from handle portion 16. Further, it can be seen that the longitudinal axes of the handle portions are generally parallel to one another.

As illustrated in FIG. 1, instrument 10 may conveniently have a thickness dimension of approximately two centimeters while its width may be approximately two and one-half centimeters as shown in FIG. 2. Smaller dimensions could readily be provided. Handle means 12 may be formed from clear plastic material and includes a cavity or recess 18 provided in first handle portion 14.

As shown in FIG. 2, recess 18 extends across the width of instrument 10 and provides an area in which a knife or blade means, generally designated at 20, and a power-driven means or motor 22 are mounted. Motor 22 may be a small electric motor and is appropriately connected to a side wall 14a of recess 18. Motor 22 includes a drive shaft 24 operatively coupled to a cam means such as cylindrical cam member 26. Motor 22 may be appropriately powered by a small battery source or suitably connected to an external power source.

With reference also directed to FIG. 3, it can be seen that blade means 20 includes a hollow cylindrical blade 28 which is coaxially mounted on a cylindrical guide means or stem 30. Stem 30 extends outwardly from an upper face of first handle portion 14, and also extends downwardly into section 14b of the first handle portion for rigid connection thereto. Stem 30 includes an elongate bore 31 which extends axially therethrough from a concave end face 32 to a bottom face 34. Concave end face 32 is dimensioned for seating against the outer curved surface of a cornea. Additionally, it can be seen that blade 28 is provided with an annular cutting edge 29.

Extending about the outer periphery of blade 28 and rigidly connected thereto is a flange or projecting member 36. Member 36 is provided with a tapered portion 36a which is coupled to one end of an arm means or link 38 having its other end connected to cam member 26 at a location offset from the longitudinal axis of shaft 24. Thus, it can be appreciated that link 38 is operatively interconnected between shaft 24 and blade 28 for imparting rotary motion from the shaft to the blade. As shown in FIG. 2, dot-dash lines A, B define an arc about which blade 28 may be oscillated by rotation of cam member 26 and link 38. This motion is thereby imparted to cutting edge 29.

With attention now directed more particularly to FIG. 3, it can be seen that a shifting means, generally designated at 40, is provided for extending and retracting blade 28 axially along stem 30. Specifically, shifting means 40 includes a cylindrical actuating element 42 extending through a bore 44 in first handle portion 14. One end of actuating element 42 is provided with an upper retaining portion having a recess or slot for receiving one end of projecting member 36. A cylindrical retainer 44 is connected to a central portion 46 and is spaced from the top of actuating element 42 a predetermined distance for accommodating reception of projecting member 36. Actuating element 42 includes a thumb engaging member 48. A biasing means such as a coil spring 50 is provided for normally urging actuating element 42 downwardly, as viewed in FIG. 3, so that cutting edge 29 is disposed adjacent to or slightly beneath the outer periphery of concave end face 32. Thus, it can be seen that upon depressing member 48, rectilinear motion will be transferred to projecting member 36 and correspondingly to blade 28 so that the blade may be selectively extended in the axial direction of stem 30. Upon release of pressure against member 48, blade 28 will be retracted.

It is to also be noted that longitudinal bore 31 is suitably connected to a tube or other conduit 52 for connection to a vacuum producing source. Further, a cover plate 54 (broken away in FIG. 2) is suitably connected to the first handle portion by appropriate screw fasteners such as shown at 56. The cover plate permits selective access to blade means 20 and shifting means 40.

Use of instrument 10 during the removal of a corneal button will now be described. Assuming that the left eye of an individual donor or recipient is to be operated upon, the surgeon will grip first handle portion 14 in his right hand and second handle portion 16 in his left hand. Blade means 20 will be positioned adjacent to the cornea with blade 28 retracted and concave end face 32 seated against the cornea. Suction is applied through conduit 52 and bore 31 so that the cornea is drawn against end face 32. Motor 22 is then actuated and blade 28 is oscillated about its longitudinal axis. This provides initial cutting action along cutting edge 29, and the surgeon then depresses element 48 so that blade 28 and cutting edge 29 effect smooth cutting action through the cornea's thickness. Because stem 30 and the handle portions are provided with clear plastic material, the surgeon can look downwardly through the stem and observe the incision and progress of the operation.

A corneal button is formed when cutting edge 29 has completely penetrated through the cornea's thickness (approximately 1 millimeter in human beings). After cutting edge 29 has cut out a corneal button, the surgeon withdraws instrument 10 after first releasing pressure on member 48 and deactivating motor 22. Because the suction has not yet been released, the corneal button remains held against concave end face 32. The button may then be transferred to a storage receptacle or used in grafting.

The above steps are initially performed on a so-called donor in order to procure a healthy corneal button. A recipient then has a defective corneal button removed and the donor's corneal button is transplanted into the recipient and sutured in place. From the above, it should be evident that instrument 10 of the present invention provides several important and distinct advantages over prior art trephine instruments. For instance, suction applied to the cornea during cutting action provides an offsetting force to pressure being exerted against the cornea during extension of blade 28. Thus, cutting edge 29 cuts through the cornea's thickness and extends into the anterior chamber without appreciably deforming the corneal button. Adding to the non-deformation of the button is the fact that concave end face 32 provides a curved surface for seating against the cornea.

Another advantage of the present invention resides in the fact that the instrument is constructed so that a surgeon may grip it with both hands and position the hands adjacent to a donor or recipient's face. Handle means 12 is provided with offset first and second handle portions 14, 16 which enable the handle means to be placed adjacent a donor or recipient's eye. No supporting table or bench is required. The surgeon can grip instrument 10 with all his fingers so that the instrument can be securely held and maintained in a steady position.

Additionally, it should be perceived that instrument 10 is equally suitable for use on either the right or left eye For instance, it can readily imagined that instrument 10, as shown in FIG. 1, could be "flip-flopped" for use on the right eye. This would result in a surgeon's right hand gripping second handle portion 16 and the left hand gripping first handle portion 14. Blade means 20 could then be positioned adjacent the right eye and interconnecting portion 17 would bypass the donor or recipient's nose so that second handle portion 16 would extend adjacent the left eye.

Another advantage of the present invention resides in the specific construction of drive shaft 24, cam member 26 and link 38 which provide oscillatory motion to blade 28 about its longitudinal axis. The oscillatory motion provides efficient cutting action for rapid and precise penetration through the thickness of a cornea. Oscillatory motion could also be provided in the direction of the blade's longitudinal axis, if desired. Further, it can be seen that precise control during the extension of blade 28 through the cornea is provided by means of shifting means 40.

Turning now to FIGS. 4 and 5 of the drawings, a second embodiment of the present invention will be described. Basically, the second embodiment is directed to a trephine instrument, generally designated at 58, which includes a removable cutting blade powered by an ultrasonic source. Instrument 58 includes an elongate handle means having interconnected first and second handle portions 60, 62, respectively. The handle portions are joined by a diagonal or interconnecting portion 64 so that their longitudinal axes are offset from each other. This construction is substantially similar to instrument 10 described for the first embodiment.

Considering FIG. 6, it can be seen that first handle portion 60 is provided with a first guide means or guide 66 recessed therewithin. Guide 66 is cylindrical and is provided with a concave end face 68 contoured to seat against a cornea. The sides of guide 66 are spaced from an outer or cylindrical surrounding wall or ring 70. An elongate bore 72 extends along the longitudinal axis of guide 66 and makes a bend outwardly through first handle portion 60 for connection to a suitable vacuum producing source.

Coaxially mounted for axial and rotational movement on guide 66 is a blade means such as cylindrical cutting blade 74. Blade 74 is coaxially mounted on guide 66 and includes an annular cutting edge 76. Further, blade 74 is provided adjacent an opposite end thereof with an annular rim 78. Rim 78 extends outwardly from sidewalls of the blade and circumscribes an outer peripheral portion.

Extending from an opposite side of first handle portion 60 is a second guide means or guide 80 formed as a cylindrical member. A retaining means, generally designated at 82, includes a cylindrical ring 84 dimensioned with an interior diameter slightly greater than the outer diameter of guide 80. Extending from a lower edge of ring 84 are a plurality of retaining members such as elongate legs 86, 88 and 90 (also see FIG. 8). Each of the legs extends through a cooperating guide slot or channel formed in first handle portion 60. For instance, considering leg 90, it can be seen that it extends downwardly through a channel 92 which extends from an upper face of first handle portion 60 downwardly into the region formed between cylindrical side wall 70 and the outer wall of blade 74. Further, each leg is provided with a recess such as shown at 94 on leg 90. The recesses receive ram 78 and interlock blade 74 and ring 84. Thus, it can seen that axial movement of ring 84 over guide 80 will impart simultaneous axial movement to blade 74. In addition, it can be seen that proper dimensioning of recesses 94 will permit blade 74 to rotate along its central axis. During such rotation, rim 78 would slide within the recesses provided on the legs.

Still considering FIG. 6 in addition to FIGS. 4 and 5, it can be seen that a shifting means, generally designated at 96 is operatively connected to retaining means 82 for selectively extending and retracting blade 74. More specifically, shifting means 96 is constructed as an actuating arm 98 pivotally connected at one end thereof to interconnecting portion 64. As can be seen in FIGS. 4, 5, arm 98 extends inwardly through a slot 100 provided in portion 64 and is pivotally connected therewithin by means of a suitable pin 102.

As can also be seen from a viewing of FIG. 8, arm 98 is provided with an opening 104 dimensioned to fit over ring 84. Extending on opposite sides of opening 104 are pins 106, 108 which extend inwardly toward ring 84 and are slidably received within elongate slots provided in the ring. For instance, as shown in FIG. 6, it can be seen that pin 106 is received within elongate slot 84a. Pin 108 is similarly inserted within an accommodating slot provided in ring 84. Thus, it can be appreciated that upon depressing arm 98 toward first handle portion 60, ring 84 will be axially displaced downwardly over guide 80 for extending blade 74 and cutting edge 76 outwardly beyond the bottom of first handle portion 60. A limit means such as an adjustable screw 110 extends through the first handle portion 60 and outwardly for having an end directed toward arm 98. The extent to which arm 98 may extend blade 74 and cutting edge 76 relative to concave end face 68 may thereby be regulated. A spring 103 normally urges arm 98 upwardly.

With respect to providing cutting action to blade 74, it is contemplated that a suitable ultrasonic means by employed. For instance, there are ultrasonic instruments manufactured with impart ultrasonic vibrations to a needle. Such a needle is used, in the present invention, to provide rotational or axial motion to blade 74. More particularly, as shown in FIGS. 4-7, an ultrasonic needle 112 is suitably mounted within first handle portion 60 and extends inwardly through ring 70 for contact with an outer surface of blade 74. Suitable ultrasonic devices contemplated for use in instrument 58 may be manufactured, for example, by Sparta Instrument Corporation of Fairfield, N.J. Needle 112 is connected by means of cord 114 to an ultrasonic frequency source. Thus, it can be seen that upon actuation of needle 112 by ultrasonic means, either rotational motion or oscillatory motion of blade 74 will be provided resulting in an extremely efficient cutting action during corneal removal.

Additionally, instrument 58 may utilize needle 112 positioned adjacent blade 74 for providing oscillation in the direction of the central axis of blade 74. Instead of rotational oscillations, longitudinal oscillations could be provided for cutting action.

Use and operation of instrument 58 by a surgeon during the removal of a corneal button will now be described. The surgeon grips first and second handle portions 60, 62 in either the right or left hand depending upon which eye is to be operated upon. As shown in FIG. 4, and assuming that the eye shown on the left is an individual's left eye, the surgeon would grip first handle portion 60 with his left hand and second handle portion 62 with the right hand. Arm 98 is biased in its upward position and screw 110 has already been adjusted to permit extension of blade 74 and cutting edge 76 for a distance of approximately one millimeter, or the thickness of a typical cornea. The surgeon then positions concave end face 68 so that it is seated against the cornea. A suitable vacuum source (not shown) applies suction to the cornea so that it is drawn against concave end face 68. The ultrasonic means is actuated and cutting motion is imparted to blade 74 by needle 112. As illustrated in FIGS. 6 and 7, rotational oscillations or rotational movement will be imparted to blade 74.

The surgeon then depresses arm 98 downwardly so that the rotating or oscillating blade makes an incision into the cornea. Arm 98 is depressed until a bottom edge thereof contacts screw 110. As previously mentioned, screw 110 has been adjusted so that blade 74 will cut through the cornea a predetermined distance. For instance, as shown in FIG. 6, dimension C would correspond to approximately one millimeter. A corneal button has then been cut from the eye and is retained against concave end face 68. The surgeon may then deactivate the ultrasonic means and remove instrument 58 away from the eye.

At this point, a particular advantage of instrument 58 becomes readily apparent. With instrument 58 removed from the eye, and blade 74 extended in the position noted by dot-dash line 74a, a lid or cap may be placed over the end of the blade. The vacuum source may then be deactivated so that the removed corneal button will be contained within the inner volume of the blade. Screw 110 is then adjusted so that arm 98 can be depressed further for extending blade 74 completely free from first handle portion 60. This position is shown in FIG. 6 as dot-dash 74b, and a cap is noted at 116 in dot-dash.

With blade 74 thus extended, legs 86, 88 and 90 may be bent slightly outwardly so that blade 74 may be released and detached from engagement with the legs. Another cap is then positioned over the other end of blade 74 and a corneal button is thereby stowed or contained within a cutting blade. Corneal buttons can thereby be quickly removed and stowed within a receptacle or container for appropriate refrigerated storage.

From the above, it can be appreciated that instrument 58 provides several distinct advantages in the removal of corneal buttons. Instrument 58 utilizes an ultrasonic means including needle 112 for imparting precise and high speed rotary or longitudinal oscillations to a cutting blade. In addition, blade 74 is removable and can be used as a storage container for the very button which it has severed from an eye. Transfer of a corneal button from a trephine instrument to a storage container is thereby quickly and efficiently provided. Additional instruments requiring time consuming operation and almost inordinate skill in removing a severed cornea are not required.

While the invention has been particularly shown and described with reference to the foregoing preferred embodiment, it will be understood by those skilled in the art that other changes in form and detail may be made therein without departing from the spirit and scope of the invention as defined in the appended claims.

It is claimed and desired to secure by Letters Patent:

1. A trephine instrument for use in surgical removal of a cornea comprising:
   elongate handle means for gripping by a surgeon with both hands when in use including first and second handle portions having their longitudinal axes laterally spaced and longitudinally offset from one another, said first and second handle portions being joined together by an interconnecting portion;
   guide means mounted on said first handle means portion including a concave end face dimensioned for seating against a cornea;
   blade means having an annular cutting edge mounted on said guide means and extending outwardly from said first handle portion;
   power-driven means operable for selectively imparting cutting motion to said blade means; and
   shifting means mounted on said handle means selectively operable for extending and retracting said blade means relative to said handle means.

2. The instrument of claim 1 wherein said guide means and said blade means are both cylindrical, said blade means being coaxially mounted on said guide means, said guide means including an elongate bore extending axially therethrough from said concave end face to the opposite end for connection to a vacuum producing source, said power-driven means including a rotatable shaft operatively interconnected to said blade means for imparting rotational motion thereto.

3. The instrument of claim 2 including arm means operatively interconnected between said shaft and said blade means for transferring rotational motion from said shaft to said blade means.

4. The instrument of claim 3 including cam means mounted on said shaft, said arm means having one end thereof connected to said cam means.

5. The instrument of claim 1 wherein said blade means includes a projecting member extending outwardly therefrom for engaging said shifting means.

6. The instrument of claim 5 wherein said shifting means includes a operable actuating element normally biased for retracting said cutting edge relative to the peripheral edge of said concave end face.

7. The instrument of claim 6 wherein said actuating element includes a portion for receiving said projecting member.

8. The instrument of claim 7 wherein said actuating element and said blade means extend outwardly from opposite sides of said first handle portion.

9. A trephine instrument for use in corneal removal comprising:
   elongate handle means for gripping by a surgeon with both hands when in use including first and second handle portions having their longitudinal axes laterally spaced and longitudinally offset from one another, said first and second handle portions being joined together by an interconnecting portion;
   cylindrical guide means mounted on said handle including a concave end face dimensioned for seating against a cornea;
   cylindrical blade means slidably and rotatably received on said guide means having an annular cutting edge, said blade means being detachably and coaxially mounted on said guide means;
   power actuated means mounted on said handle operable for selectively imparting cutting motion to said blade means; and
   shifting means including an actuating member mounted on said handle means selectively operable for extending and retracting said blade means relative to said handle means, said shifting means also including retaining members connected to said actuating member and releasably connected to said blade means.

10. The instrument of claim 9 further including limit means provided on said first handle portion selectively adjustable for permitting said retaining members to be separated from said blade means after said actuating member has been displaced a predetermined distance.

11. The instrument of claim 9 wherein said retaining members extend into said first handle portion.

12. The instrument of claim 9 wherein said power-actuated means includes ultrasonic means operable for selectively oscillating said blade means and imparting cutting motion thereto 13. A trephine instrument for use in corneal removal comprising:
   elongate handle means for gripping by a surgeon with both hands when in use;
   cylindrical blade means having an annular cutting edge, said blade means being detachably mounted on said handle;
   ultrasonic means mounted on said handle including a needle operable for contacting the outer surface of said blade means to thereby selectively impart cutting motion to said blade means; and
   shifting means mounted on said handle selectively operable for extending and retracting said blade means relative to said handle means, said shifting means being detachably connected to said blade means.

14. The instrument of claim 13 wherein said handle means includes first and second handle portions having their longitudinal axes offset from each other, said first and second handle portions being joined together by an interconnecting portion.

15. The instrument of claim 14 wherein said shifting means includes retaining members releasably connected to said blade means.

16. The instrument of claim 15 wherein said retaining members extend into said first handle portion and are shiftable to extend said blade means to a position externally of said handle means.

* * * * *